United States Patent
Konishi et al.

(10) Patent No.: US 12,006,391 B2
(45) Date of Patent: *Jun. 11, 2024

(54) MEDICAL RUBBER COMPOSITION, MEDICAL RUBBER PART, AND PRE-FILLABLE SYRINGE

(71) Applicant: Sumitomo Rubber Industries, Ltd., Kobe (JP)

(72) Inventors: Hirofumi Konishi, Kobe (JP); Toshikazu Kondo, Kobe (JP); Masayoshi Kashibe, Kobe (JP); Hideyuki Shigemoto, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/860,124

(22) Filed: Jul. 8, 2022

(65) Prior Publication Data

US 2023/0008859 A1    Jan. 12, 2023

(30) Foreign Application Priority Data

Jul. 8, 2021    (JP) .................. 2021-113756

(51) Int. Cl.
| | |
|---|---|
| *C08F 36/06* | (2006.01) |
| *A61M 5/32* | (2006.01) |
| *C08F 210/10* | (2006.01) |
| *C08F 236/08* | (2006.01) |
| *C08K 3/36* | (2006.01) |
| *C08K 5/14* | (2006.01) |
| *C08K 5/3492* | (2006.01) |

(52) U.S. Cl.
CPC ............ *C08F 36/06* (2013.01); *A61M 5/3202* (2013.01); *C08F 210/10* (2013.01); *C08F 236/08* (2013.01); *C08K 3/36* (2013.01); *C08K 5/14* (2013.01); *C08K 5/3492* (2013.01); *C08K 2201/006* (2013.01); *C08K 2201/019* (2013.01)

(58) Field of Classification Search
CPC ...... C08F 36/06; C08F 210/10; C08F 236/08; A51M 6/3202; C08K 5/3492; C08K 2201/006; C08K 2201/019
See application file for complete search history.

(56) References Cited

U.S. PATENT DOCUMENTS

| | | | | |
|---|---|---|---|---|
| 5,994,465 | A * | 11/1999 | Sudo .................... | C08K 5/3415 |
| | | | | 525/105 |
| 2017/0296757 | A1* | 10/2017 | Maeda ................ | A61M 5/3202 |

FOREIGN PATENT DOCUMENTS

| | | |
|---|---|---|
| JP | 2001-340425 A | 12/2001 |
| JP | 2013-112703 A | 6/2013 |
| JP | 2015-62564 A | 4/2015 |

* cited by examiner

*Primary Examiner* — Ling Siu Choi
*Assistant Examiner* — Andrea Wu
(74) *Attorney, Agent, or Firm* — XSENSUS LLP

(57) ABSTRACT

A medical rubber composition can contain, comprise, consist, or consist essentially of: (a) an isobutylene-isoprene rubber: (b) a diene-based rubber; and a silica having a BET specific surface area not lower than 130 m²/g. An amount of (a) the isobutylene-isoprene rubber contained in 100 parts by mass of a rubber component composed of (a) the isobutylene-isoprene rubber and (b) the diene-based rubber can be larger than 30 parts by mass and smaller than 55 parts by mass.

19 Claims, 2 Drawing Sheets

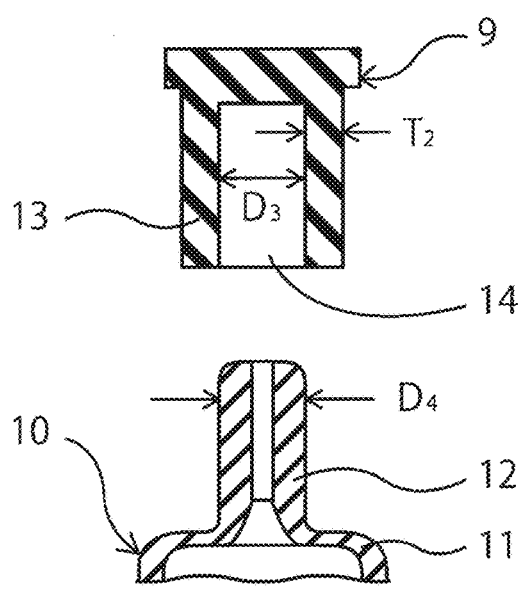
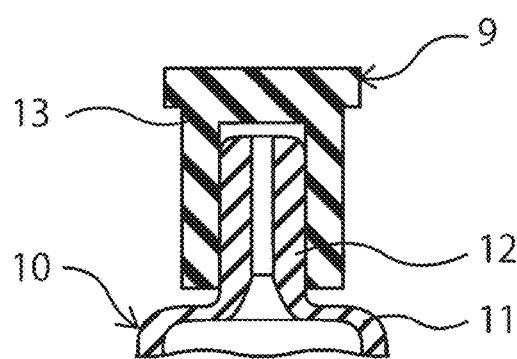
FIG. 1A                    FIG. 1B

MEDICAL RUBBER COMPOSITION, MEDICAL RUBBER PART, AND PRE-FILLABLE SYRINGE

CROSS-REFERENCE TO RELATED APPLICATION

The present application claims priority to Japanese Patent App. No. 2021-113756 filed Jul. 8, 2021. The entire content and disclosure of the foregoing application is incorporated herein by reference.

BACKGROUND

Field

The present disclosure relates to a medical rubber composition, a medical rubber part in which the medical rubber composition has been used, and a pre-fillable syringe. More specifically, the present disclosure relates to a technology that can enhance gas permeability of the medical rubber part or otherwise provide a medical rubber part with enhanced gas permeability.

Background Art

Use of prefilled syringes having sterilized syringe barrels filled with drug solutions in advance tends to be expanded in recent years from the viewpoint of prevention of medical error, handiness during usage, improvement in hygiene, and the like. Nozzle caps may be attached to nozzle-side ends of the syringe barrels of the prefilled syringes in order to ensure liquid-tightness, gas-tightness, sterility, and the like.

Examples of the prefilled syringes include a needle-equipped syringe in which a needle is embedded in a nozzle of a syringe barrel in advance, and a non-needle-equipped syringe in which, at the time of usage thereof, a nozzle cap is detached and an injection needle is set. Examples of the nozzle cap include a needle-shielding-type nozzle cap having a needle piercing portion for a needle-equipped syringe and configured to cover a nozzle in a state where the needle pierces the needle piercing portion by several millimeters, and a nozzle cap of a type configured to cover a nozzle of a non-needle-equipped syringe (see Japanese Laid-Open Patent Publication No. 2013-112703, Japanese Laid-Open Patent Publication No. 2001-340425, Japanese Laid-Open Patent Publication No. 2015-62564, or the like).

The prefilled syringe may be packaged and shipped as a product after: sterilization with ethylene oxide gas (EOG), sterilization with vapor, radiation sterilization with gamma ray, or the like, is performed in a state where a nozzle of a syringe barrel not having yet been filled with a drug solution is covered by a nozzle cap; then the syringe barrel is filled with a drug solution in a sterile condition; and then a sterilized gasket is plugged.

In gas sterilization with EOG or vapor, it may be required to send a gas such as EOG or vapor through rubber forming a nozzle cap so as to permeate the inside of the nozzle cap so that in the case of, for example, a needle-equipped syringe, the entirety of the needle including the tip thereof piercing the needle piercing portion, a nozzle, and the like, can be sterilized.

After sterilization with EOG, it may be required to be able to swiftly remove, through deaeration, residues such as ethylene oxide used for the sterilization, and ethylene glycol and ethylene chlorohydrin which are secondary products of the ethylene oxide. Meanwhile, after sterilization with vapor, it may be required to be able to swiftly remove adsorbed water through drying.

Japanese Patent No. 3193895 describes a rubber plug for a pharmaceutical agent container, the rubber plug being characterized by being obtained by blending 5 to 25 parts by weight of fine powder of polyethylene with an ultrahigh molecular weight per 100 parts by weight of halogenated isobutylene-isoprene rubber, and vulcanizing the resultant halogenated isobutylene-isoprene rubber by using at least one of 2-substituted-4,6-dithiol-s-triazine derivatives or by using an organic peroxide, in the absence of a zinc compound.

International Publication No. WO2016/052037 describes a nozzle cap for a prefilled syringe, the nozzle cap being made from a rubber composition that contains a rubber component obtained by blending a diene-based rubber and a non-diene-based rubber such that the proportion of the diene-based rubber in a total amount of, i.e., 100 parts by mass of, both rubbers is not smaller than 20 parts by mass and not larger than 70 parts by mass.

Medical rubber plugs for, for example, tightly closing an opening of a syringe may be required to have many characteristics such as non-oozing characteristics, high cleanability, chemical resistance, resistance to needle piercing, self-sealability, and high slidability. The medical rubber plugs should, in consideration of use thereof, have quality characteristics that comply with the regulations stipulated in, for instance, "Test for Rubber Closure for Aqueous Infusions" of the 17th edition of the Japanese Pharmacopoeia.

A medical rubber part may be produced as follows. That is, an unvulcanized rubber sheet can be made from a medical rubber composition, and the unvulcanized rubber sheet can be pressed so as to be molded. The molded sheet having been subjected to the pressing can be taken out from the mold, and the molded sheet can be punched, whereby a medical rubber part can be produced. If the strength of the molded product (molded sheet) is low, the molded sheet might be broken when the molded sheet is taken out from the mold. Consequently, fragments of the vulcanized rubber may remain on the mold, whereby a problem arises in that productivity is reduced. In addition, the broken molded sheet cannot be punched either. In addition, if a medical rubber composition having poor moldability is used, a weld line may be generated on a molded product. A molded product having a weld line may give an impression that the molded product has a poor quality as a medical rubber part.

SUMMARY

A medical rubber composition according to the present disclosure can contain: (a) an isobutylene-isoprene rubber; (b) a diene-based rubber; and a silica having a BET specific surface area not lower than 130 $m^2/g$.

An amount of (a) the isobutylene-isoprene rubber contained in 100 parts by mass of a rubber component composed of (a) the isobutylene-isoprene rubber and (b) the diene-based rubber can be larger than 30 parts by mass and smaller than 55 parts by mass.

BRIEF DESCRIPTION OF THE DRAWINGS

FIG. 1A and FIG. 1B are each a diagram for explaining a medical rubber part (e.g., nozzle cap) according to one or more embodiments of the present disclosure.

DETAILED DESCRIPTION

Figure 2A:
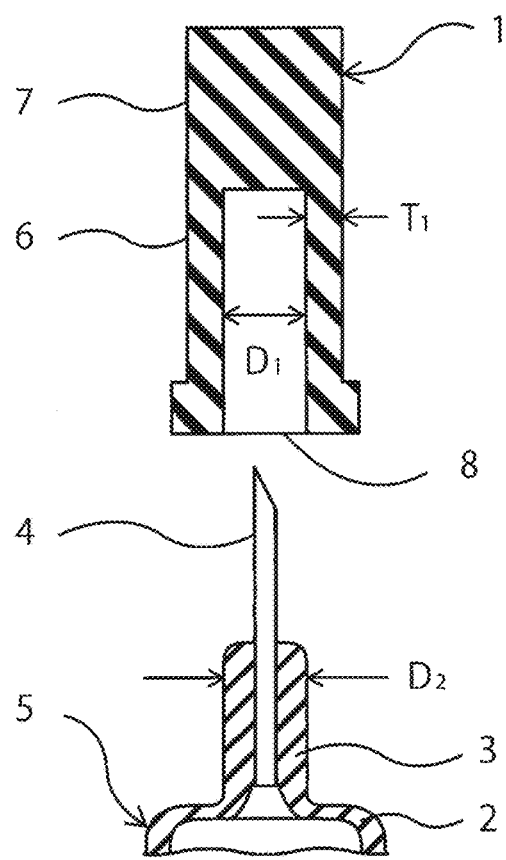
FIG. 2A and FIG. 2B are each a diagram for explaining a medical rubber part (e.g., nozzle cap) according to one or more embodiments of the present disclosure.

A medical rubber composition according to one or more embodiments of the present disclosure can contain: (a) an isobutylene-isoprene rubber: (b) a diene-based rubber; and a silica having a BET specific surface area not lower than 130 m$^2$/g, wherein an amount of (a) the isobutylene-isoprene rubber contained in 100 parts by mass of a rubber component composed of (a) the isobutylene-isoprene rubber and (b) the diene-based rubber is larger than 30 parts by mass and smaller than 55 parts by mass. According to one or more embodiments, the medical rubber composition, or portions thereof, can comprise, consist of, or consist essentially of the (a) and the (b) and the silica.

Firstly, (a) the isobutylene-isoprene rubber will be described. As the isobutylene-isoprene rubber, for example, a copolymer obtained by polymerizing isobutylene and a relatively small amount of isoprene can be implemented or used.

The isobutylene-isoprene rubber can be a halogenated isobutylene-isoprene rubber. Examples of the halogenated isobutylene-isoprene rubber include: chlorinated isobutylene-isoprene rubbers; brominated isobutylene-isoprene rubbers; bromides of a copolymer of isobutylene and p-methylstyrene; and the like. As the halogenated isobutylene-isoprene rubber, a chlorinated isobutylene-isoprene rubber or a brominated isobutylene-isoprene rubber may be implemented or used. The chlorinated isobutylene-isoprene rubber or the brominated isobutylene-isoprene rubber may be obtained by, for example, causing a reaction in which: chlorine or bromine is added to an isoprene structural moiety (specifically, a double bond and/or a carbon atom adjacent to the double bond) in an isobutylene-isoprene rubber; or the isoprene structural moiety may be substituted with chlorine or bromine.

The halogen content of the halogenated isobutylene-isoprene rubber may be, for instance, not lower than 0.5% by mass, such as not lower than 1% by mass, or not lower than 1.5% by mass. Meanwhile, the halogen content may be, for instance, not higher than 5% by mass, such as not higher than 4% by mass, or not higher than 3% by mass.

Specific examples of the chlorinated isobutylene-isoprene rubber include at least one of: CHLOROBUTYL1066 [stabilizer: NS, halogen content: 1.26%, Mooney viscosity: 38 ML$_{1+8}$ (125° C.), specific gravity: 0.92] manufactured by JAPAN BUTYL Co., Ltd.; LANXESS X_BUTYL CB1240 manufactured by LANXESS; and the like.

Specific examples of the brominated isobutylene-isoprene rubber include at least one of: BROMOBUTYL2255 [stabilizer: NS, halogen content: 2.0%, Mooney viscosity: 46 ML$_{1+8}$ (125° C.), specific gravity: 0.93] manufactured by JAPAN BUTYL Co., Ltd.: LANXESS X_BUTYL BBX2 manufactured by LANXESS; and the like.

The medical rubber composition according to one or more embodiments of the present disclosure can contain (b) the diene-based rubber as a rubber component. The diene-based rubber may be a rubber that is obtained by polymerizing a diene monomer and that has a double bond in the main chain thereof. In one or more embodiments of the present disclosure, although (a) the isobutylene-isoprene rubber which is a copolymer obtained by polymerizing isobutylene and a small amount of isoprene has the small amount of isoprene copolymerized, (a) the isobutylene-isoprene rubber may not be regarded as a diene-based rubber.

Examples of the diene-based rubber include natural rubber (NR), isoprene rubber (IR), polybutadiene (BR), styrene-butadiene rubber (SBR), chloroprene rubber (CR), and acrylonitrile-butadiene rubber (NBR). These diene-based rubbers may be used singly, or two or more of these diene-based rubbers may be used in combination.

In the present disclosure, (b) a poly butadiene-containing diene-based rubber may be used as the diene-based rubber. The polybutadiene content of the diene-based rubber may be, for instance, not lower than 50% by mass, such as not lower than 70% by mass, or not lower than 90% by mass. A mode in which the diene-based rubber contains only polybutadiene may be implemented or used.

In the medical rubber composition according to one or more embodiments of the present disclosure, the amount of (a) the isobutylene-isoprene rubber contained in 100 parts by mass of the rubber component composed of (a) the isobutylene-isoprene rubber and (b) the diene-based rubber may be, for instance, larger than 30 parts by mass, such as not smaller than 31 parts by mass, or not smaller than 33 parts by mass. Meanwhile, the amount may be, for instance, smaller than 55 parts by mass, such as not larger than 54 parts by mass, or not larger than 52 parts by mass. If the amount of (a) the isobutylene-isoprene rubber falls within the aforementioned range(s), it may be possible to increase gas permeability while maintaining excellent non-oozing characteristics. As a result, for example, the time taken to perform a gas sterilization step for a pre-fillable syringe not having yet been filled with a drug solution can be shortened.

The medical rubber composition according to the present disclosure can contain a crosslinking agent (c), for instance, a peroxide-based crosslinking agent (c1). The peroxide-based crosslinking agent (c1) may be an agent that is blended mainly for causing crosslinking in (b) the diene-based rubber.

Specific examples of the peroxide-based crosslinking agent (c1) include dialkyl peroxides, peroxyesters, peroxyketals, hydroperoxides, and the like. Examples of the dialkyl peroxides include di(2-t-butylperoxyisopropyl)benzene, dicumyl peroxide, 2,5-dimethyl-2,5-di(t-butylperoxy)hexane, t-butylcumyl peroxide, di-t-hexyl peroxide, di-t-butyl peroxide, 2,5-dimethyl-2,5-di(t-butylperoxy)hexyne-3, and the like. Examples of the peroxyesters include t-butylperoxymaleate, t-butylperoxy-3,3,5-trimethylcyclohexanoate, t-butylperoxylaurate, t-butylperoxyisopropyl monocarbonate, t-hexylperoxybenzoate, 2,5-dimethyl-2,5-di(benzoylperoxy)hexane, t-butylperoxvacetate, t-butylperoxybenzoate, and the like. Examples of the peroxyketals include 1,1-di(t-hexylperoxy)-3,3,5-trimethylcyclohexane, 1,1-di(t-hexylperoxy)cyclohexane, 1,1-di(t-butylperoxy)-2-methylcyclohexane, 1,1-di(t-butylperoxy)cyclohexane, 2,2-di(t-butylperoxy)butane, n-butyl-4,4-di(t-butylperoxy)valerate, 2,2-di(4,4-di(t-butylperoxy)cyclohexyl)propane, and the like. Examples of the hydroperoxides include p-menthane hydroperoxide, diisopropylbenzene hydroperoxide, and the like. These organic peroxides may be used singly, or two or more of these organic peroxides may be used in combination.

In the medical rubber composition according to one or more embodiments of the present disclosure, the amount of (c1) the peroxide-based crosslinking agent contained per 100 parts by mass of the rubber component composed of (a) the isobutylene-isoprene rubber and (b) the diene-based rubber may be, for instance, not smaller than 0.05 parts by mass, such as not smaller than 0.1 parts by mass, or not smaller than 0.15 parts by mass. Meanwhile, the amount may be, for instance, not larger than 7 parts by mass, such as not larger than 5 parts by mass, or not larger than 2 parts by mass. The reason for this can be because, if the amount of the the peroxide-based crosslinking agent (c1) falls within the aforementioned range, softening of the isobutylene-isoprene rubber component can be suppressed, and non-oozing characteristics can be maintained.

The medical rubber composition according to one or more embodiments of the present disclosure may contain a crosslinking agent other than the peroxide-based crosslinking agent (c1), unless the advantageous effect of the present disclosure is impaired. Examples of the crosslinking agent other than the peroxide-based crosslinking agent (c1) can include a triazine derivative (c2), a sulfur (c3), a metal oxide (c4), a resin crosslinking agent (c5), and the like. These crosslinking agents may be used singly, or two or more of these crosslinking agents may be used in combination.

The medical rubber composition according to one or more embodiments of the present disclosure can contain a triazine derivative (c2). The triazine derivative can act as a crosslinking agent on (a) the isobutylene-isoprene rubber. Examples of the triazine derivative include a compound represented by a general formula (1).

[Chem. 1]

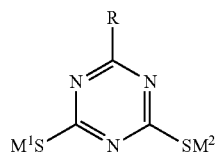

(1)

[in the formula, R represents —SH, —OR$^1$, —SR$^2$, —NHR$^3$, or —NR$^4$R$^5$ (R$^1$, R$^2$, R$^3$, R$^4$, and R$^5$ each represent an alkyl group, an alkenyl group, an aryl group, an aralkyl group, an alkylaryl group, or a cycloalkyl group. R$^4$ and R$^5$ may be identical to each other or different from each other.). M$^1$ and M$^2$ each represent H, Na, Li, K, ½Mg, ½Ba, ½Ca, an aliphatic primary, secondary, or tertiary amine, a quaternary ammonium salt, or a phosphonium salt. M$^1$ and M$^2$ may be identical to each other or different from each other.]

In the general formula (1), examples of the alkyl group include alkyl groups having 1 to 12 carbon atoms, such as a methyl group, an ethyl group, an n-propyl group, an isopropyl group, an n-butyl group, an isobutyl group, a tert-butyl group, an n-pentyl group, an isopentyl group, a tert-pentyl group, an n-hexyl group, a 1,1-dimethylpropyl group, an octyl group, an isooctyl group, a 2-ethylhexyl group, a decyl group, and a dodecyl group. Examples of the alkenyl group include alkenyl groups having 1 to 12 carbon atoms, such as a vinyl group, an allyl group, a 1-propenyl group, an isopropenyl group, a 2-butenyl group, a 1,3-butadienyl group, and a 2-pentenyl group. Examples of the aryl group include monocyclic aromatic hydrocarbon groups and condensed polycyclic aromatic hydrocarbon groups, and examples thereof include: aryl groups having 6 to 14 carbon atoms, such as a phenyl group, a naphthyl group, an anthryl group, a phenanthryl group, and an acenaphthylenyl group; and the like. Examples of the aralkyl group include aralkyl groups having 7 to 19 carbon atoms, such as a benzyl group, a phenethyl group, a diphenylmethyl group, a 1-naphthylmethyl group, a 2-naphthylmethyl group, a 2,2-diphenylethyl group, a 3-phenylpropyl group, a 4-phenylbutyl group, a 5-phenylpentyl group, a 2-biphenylylmethyl group, a 3-biphenylylmethyl group, and a 4-biphenylylmethyl group. Examples of the alkylaryl group include alkylaryl groups having 7 to 19 carbon atoms, such as a tolyl group, a xylyl group, and an octylphenyl group. Examples of the cycloalkyl group include: cycloalkyl groups having 3 to 9 carbon atoms, such as a cyclopropyl group, a cyclobutyl group, a cyclopentyl group, a cyclohexyl group, a cycloheptyl group, a cyclooctyl group, and a cyclononyl group; and the like.

Specific examples of the triazine derivative represented by the general formula (1) include 2,4,6-trimercapto-s-triazine, 2-methylamino-4,6-dimercapto-s-triazine, 2-(n-butylamino)-4,6-dimercapto-s-triazine, 2-octylamino-4,6-dimercapto-s-triazine, 2-propylamino-4,6-dimercapto-s-triazine, 2-diallylamino-4,6-dimercapto-s-triazine, 2-dimethylamino-4,6-dimercapto-s-triazine, 2-dibutylamino-4,6-dimercapto-s-triazine, 2-di(iso-butylamino)-4,6-dimercapto-s-triazine, 2-dipropylamino-4,6-dimercapto-s-triazine, 2-di(2-ethylhexyl)amino-4,6-dimercapto-s-triazine, 2-dioleylamino-4,6-dimercapto-s-triazine, 2-laurylamino-4,6-dimercapto-s-triazine, 2-anilino-4,6-dimercapto-s-triazine, and sodium salts and disodium salts thereof.

Among these triazine derivatives, 2,4,6-trimercapto-s-triazine, 2-dialkylamino-4,6-dimercapto-s-triazine, and 2-anilino-4,6-dimercapto-s-triazine are preferable, and 2-dibutylamino-4,6-dimercapto-s-triazine may be preferable since 2-dibutylamino-4,6-dimercapto-s-triazine can be relatively easy to obtain.

Other examples of the triazine derivatives include one or more of 6-[bis(2-ethylhexyl)amino]-1,3,5-triazine-2,4-dithiol, 6-diisobutylamino-1,3,5-triazine-2,4-dithiol, 6-dibutylamino-1,3,5-triazine-2,4-dithiol, 6-dibutylamino-1,3,5-triazine-2,4-dithiol monosodium, 6-anilino-1,3,5-triazine-2,4-dithiol, 1,3,5-triazine-2,4,6-trithiol, and the like.

In one or more embodiments of the present disclosures, these triazine derivatives may be used singly, or two or more of these triazine derivatives may be used in combination.

In one or more embodiments of the present disclosure, the peroxide-based crosslinking agent (c1) and the triazine derivative (c2) may be used in combination. In this case, the mass ratio of the peroxide-based crosslinking agent (c1) to the triazine derivative (c2) can be, for instance, not lower than 0.05, such as not lower than 0.1, or not lower than 0.15. Meanwhile, the mass ratio can be, for instance, not higher than 0.5, such as not higher than 0.25, or not higher than 0.2. The reason for this can be because, if the mass ratio of the peroxide-based crosslinking agent (c1) to the triazine derivative (c2) can be set to fall within the aforementioned range, it can be possible to achieve both low-oozing characteristics and a degree of crosslinking necessary for a blended polymer.

Examples of the sulfur (c3) used as a crosslinking agent can include powdered sulfur, finely powdered sulfur, precipitated sulfur, colloidal sulfur, sulfur chloride, and the like.

Examples of the metal oxide (c4) used as a crosslinking agent can include magnesium oxide, calcium oxide, zinc oxide, copper oxide, and the like.

Examples of the resin crosslinking agent (c5) can include alkylphenol-formaldehyde resins such as an alkylphenol-formaldehyde resin, a thermally reactive phenol resin, a phenol dialcohol-based resin, a bisphenol resin, and a thermally reactive bromomethyl alkylated phenol resin.

The medical rubber composition according to one or more embodiments of the present disclosure may contain no vulcanization accelerator. That is, the medical rubber composition according to embodiments of the disclosed subject matter may not have or include any vulcanization accelerator. The reason for this can be because a vulcanization accelerator could remain in a rubber product obtained as a final product and could ooze into a drug solution inside a syringe or a vial. Examples of the vulcanization accelerator include guanidine-based accelerators (e.g., diphenylguanidine), thiuram-based accelerators (e.g., tetramethylthiuram disulfide and tetramethylthiuram monosulfide), dithiocarbamate-based accelerators (e.g., zinc dimethyldithiocarbamate), thiazole-based accelerators (e.g., 2-mercaptobenzothiazole and dibenzothiazyl disulfide), and sulfenamide-based accelerators (N-cyclohexyl-2-benzothiazole sulfenamide and N-t-butyl-2-benzothiazole sulfenamide).

The medical rubber composition according to one or more embodiments of the present disclosure may contain a hydrotalcite. The hydrotalcite can function as an anti-scorching agent at the time of causing crosslinking in the halogenated isobutylene-isoprene rubber and can also provide a function of preventing increase in permanent strain upon compression in the medical rubber part. Further, the hydrotalcite can also function as an acid acceptor to absorb chlorine-based gas and bromine-based gas, which may have been generated upon crosslinking of the halogenated isobutylene-isoprene rubber, and prevent occurrence of crosslinking inhibition due to these gases or the like. The aforementioned magnesium oxide can also function as an acid acceptor.

Examples of the hydrotalcite include one or more of Mg—Al-based hydrotalcites such as $Mg_{4.5}Al_2(OH)_{13}CO_3 \cdot 3.5H_2O$, $Mg_{4.5}Al_2(OH)_{13}CO_3$, $Mg_4Al_2(OH)_{12}CO_3 \cdot 3.5H_2O$, $Mg_6Al_2(OH)_{16}CO_3 \cdot 4H_2O$, $Mg_5Al_2(OH)_{14}CO_3 \cdot 4H_2O$, $Mg_3Al_2(OH)_{10}CO_3 \cdot 1.7H_2O$, and the like.

Specific examples of the hydrotalcite include DHT-4A (registered trademark)-2 manufactured by Kyowa Chemical Industry Co., Ltd., and the like.

If a hydrotalcite is used as an acid acceptor in the medical rubber composition, the hydrotalcite can be used in combination with MgO. In this case, the blending amount of the hydrotalcite can be considered in terms of the total amount of the acid acceptors (hydrotalcite and MgO). The total amount of the acid acceptors (hydrotalcite and MgO) contained per 100 parts by mass of the rubber component composed of (a) the isobutylene-isoprene rubber and (b) the diene-based rubber can be, for instance, not smaller than 0.5 parts by mass such as not smaller than 1 part by mass. Meanwhile, the total amount can be, for instance, not larger than 15 parts by mass such as not larger than 10 parts by mass. The reason for this can be because, if the total amount of the acid acceptors (hydrotalcite and MgO) falls within the aforementioned range, generation of rust on a mold or the like can be suppressed, and defects that raw materials themselves turn into a white-spotted unwanted object can be reduced.

The medical rubber composition according to one or more embodiments of the present disclosure may contain a co-crosslinking agent. The co-crosslinking agent can be considered to form crosslinks by acting on radicals, of (b) the diene-based rubber, that can be formed by the peroxide-based crosslinking agent.

The co-crosslinking agent can be a polyfunctional (meth)acrylate compound. The polyfunctional (meth)acrylate compound can be a difunctional or higher-functional (meth)acrylate-based compound or a trifunctional or higher-functional (meth)acrylate-based compound. Meanwhile, the polyfunctional (meth)acrylate compound can be an octa-functional or lower-functional (meth)acrylate-based compound or a hexafunctional or lower-functional (meth)acrylate-based compound. Examples of the difunctional or higher-functional (meth)acrylate compound can include a compound having at least two acryloyl groups and/or methacryloyl groups. The term "(meth)acrylate" can mean "acrylate" and/or "methacrylate."

Examples of the difunctional or higher-functional (meth) acrylate-based compound can include di(meth)acrylate of polyethylene glycol, 1,4-butanediol di(meth)acrylate, 1,6-hexanediol di(meth)acrylate, 1,9-nonanediol di(meth)acrylate, trimethylolpropane tri(meth)acrylate, trimethylolethane tri(meth)acrylate, pentaerythritol tri(meth)acrylate, pentaerythritol tetra(meth)acrylate, glycerin tri(meth)acrylate, dipentaerythritol tri(meth)acrylate, dipentaerythritol tetra (meth)acrylate, dipentaerythritol penta(meth)acrylate, dipentaerythritol hexa(meth)acrylate, tripentaerythritol tetra (meth)acrylate, tripentaerythritol penta(meth)acrylate, tripentaerythritol hexa(meth)acrylate, tripentaerythritol hepta (meth)acrylate, and the like. These co-crosslinking agents may be used singly, or two or more of these co-crosslinking agents may be used in combination.

In the medical rubber composition according to one or more embodiments of the present disclosure, the amount of the co-crosslinking agent contained per 100 parts by mass of the rubber component composed of (a) the isobutylene-isoprene rubber and (b) the diene-based rubber may be, for instance, not smaller than 0.1 parts by mass, such as not smaller than 0.4 parts by mass or not smaller than 0.6 parts by mass. Meanwhile, the amount can be, for instance, not larger than 10 parts by mass, such as not larger than 5 parts by mass, or not larger than 3 parts by mass. The reason for this can be because, if the amount of the co-crosslinking agent falls within the aforementioned range, softening of the isobutylene-isoprene rubber component can be suppressed, and non-oozing characteristics can be maintained.

The medical rubber composition according to the present disclosure can contain, as a filler (d), a silica having a BET specific surface area, for instance, not lower than 130 m$^2$/g. If the silica is contained, the strength of an obtained medical rubber product can take a favorable value.

The BET specific surface area of the silica can be, for instance, not lower than 130 m$^2$/g, such as not lower than 140 m$^2$/g, not lower than 150 m$^2$/g, or not lower than 160 m$^2$/g. Meanwhile, the BET specific surface area can be, for instance, not higher than 300 m$^2$/g, such as not higher than 240 m$^2$/g, or not higher than 200 m$^2$/g. If the specific surface area of the silica falls within the aforementioned range, the strength of the obtained medical rubber product can take a favorable value.

The blending amount of the silica per 100 parts by mass of the rubber component composed of (a) the isobutylene-isoprene rubber and (b) the diene-based rubber can be, for instance, not smaller than 2 parts by mass such as not smaller than 3 parts by mass. Meanwhile, the blending amount can be, for instance, smaller than 10 parts by mass, such as not larger than 9 parts by mass, or not larger than 7 parts by mass. If the amount of the silica is not smaller than 2 parts by mass, the strength of the obtained medical rubber product can take a favorable value. Meanwhile, if the amount of the silica is smaller than 10 parts by mass, a pattern (weld line) can be inhibited from being formed, at the time of molding, on the surface of the obtained medical rubber product.

In the medical rubber composition according to one or more embodiments of the present disclosure, a filler other than silica may be blended. Examples of the filler (d) can include inorganic fillers such as clay and talc, resin powders of olefin-based resins, resin powders of styrene-based elastomers, and resin powders of ultrahigh-molecular-weight polyethylene (UHMWPE). Among these fillers, an inorganic filler can be clay or talc can be implemented or provided. The filler can have a function of adjusting the rubber hardness of a medical rubber part and can function also as an extender for reducing manufacturing cost for a medical rubber part.

Examples of the clay can include calcined clay and kaolin clay. Specific examples of the clay include SILLITIN (registered trademark) Z manufactured by Hoffmann Mineral GmbH, SATINTONE (registered trademark) W manufactured by Engelhard Corporation, NN kaolin clay manufactured by Tsuchiya Kaolin Industry Co., Ltd., PoleStar200R manufactured by Imerys Specialties Japan Co. Ltd., and the like.

Specific examples of the talc include High toron A manufactured by Takehara Kagaku Kogyo Co., Ltd., MICRO ACE (registered trademark) K-1 manufactured by Nippon Talc Co., Ltd., MISTRON (registered trademark) Vapor manufactured by Imerys Specialties Japan Co., Ltd., and the like.

The amount of the filler other than silica can be set as appropriate according to a target rubber hardness of a medical rubber part and the like. The amount of the filler other than silica contained per 100 parts by mass of the rubber component composed of (a) the isobutylene-isoprene rubber and (b) the diene-based rubber can be, for example, not smaller than 10 parts by mass, such as not smaller than 15 parts by mass, or not smaller than 20 parts by mass. Meanwhile, the amount can be, for instance, not larger than 40 parts by mass, such as not larger than 35 parts by mass, or not larger than 30 parts by mass.

In the medical rubber composition according to the present disclosure, a colorant such as titanium oxide or carbon black, stearic acid or low-density polyethylene (LDPE) as a lubricant, polyethylene glycol as a processing aid or as a crosslinking activator, a plasticizer (for example, paraffin oil), and the like may further be blended in appropriate proportions.

The inorganic filler content (% by mass) of the medical rubber composition according to one or more embodiments of the present disclosure can be, for instance, not lower than 10%, such as not lower than 15%, or not lower than 20%. Meanwhile, the inorganic filler content can be, for instance, not higher than 45%, such as not higher than 40%, or not higher than 35%. The reason for this can be because, if the inorganic filler content falls within the aforementioned range, it can become possible to achieve both moldability and kneadability and it can also become possible to reduce the concentration of impurities. Examples of the inorganic filler include silica, kaolin, magnesium oxide, and the like, but do not include carbon black.

Embodiments of the present disclosure can encompass a medical rubber part molded from the medical rubber composition according to one or more embodiments of the present disclosure. Examples of the medical rubber part according to one or more embodiments of the present disclosure include: rubber plugs and sealing members of containers for various medical preparations such as a liquid preparation, a powder preparation, and a freeze-dried preparation; slidable parts and sealing parts such as rubber plugs for vacuum blood collection tubes, and plunger stoppers and nozzle caps for pre-fillable syringes; and the like.

The medical rubber composition according to one or more embodiments of the present disclosure may be obtained by kneading (a) the isobutylene-isoprene rubber, (b) the diene-based rubber, the silica, and other blending materials to be added as necessary. The kneading can be performed by using, for example, an open roll, a sealed-type kneader, or the like. A kneaded product is preferably molded in the shape of a ribbon, the shape of a sheet, the shape of a pellet, or the like, and can be molded in the shape of a sheet.

If the kneaded product having the shape of a ribbon, the shape of a sheet, or the shape of a pellet is press-molded, a medical rubber part having a desired shape can be obtained. A crosslinking reaction in the medical rubber composition progresses during the pressing. The temperature in the molding can be, for example, not lower than 130° C. such as not lower than 140° C. Meanwhile, the temperature can be, for instance, not higher than 200° C. such as not higher than 190° C. The time for the molding can be, for instance, not shorter than 2 minutes such as not shorter than 3 minutes. Meanwhile, the time can be, for instance, not longer than 60 minutes such as not longer than 30 minutes. The pressure for the molding can be, for instance, not lower than 0.1 MPa such as not lower than 0.2 MPa. Meanwhile, the pressure can be not higher than 10 MPa such as not higher than 8 MPa.

Unnecessary portions can be cut off and removed from the molded product after the press-molding, such that the molded product can have a predetermined shape. The obtained molded product can be cleaned, sterilized, dried, and packaged to produce a medical rubber part.

In addition, a resin film may be stacked on and integrated with the medical rubber part. Examples of the resin film can include films made from inactive resins such as polytetrafluoroethylene (PTFE), tetrafluoroethylene-ethylene copolymer (ETFE), modified products thereof, and ultra-high molecular weight polyethylene (UHMWPE).

The resin film may only have to be, for example, press-molded in a state of being superposed on the rubber composition having the shape of a sheet such that the resin film is integrated with the medical rubber part formed after the press-molding.

The medical rubber part according to one or more embodiments of the present disclosure can have a rubber hardness indicated as a type A durometer hardness (Shore A hardness) measured in compliance with the measurement method described in "Rubber, vulcanized or thermoplastic—Determination of hardness—Part 3: Durometer method" of the Japanese Industrial Standard JIS K6253-3: 2012. The type A durometer hardness (Shore A hardness) can be, for instance, not lower than 35 such as not higher than 70.

The Shore A hardness of a slidable or sealing part such as a plunger stopper or a nozzle cap for a pre-fillable syringe can be, for instance, not lower than 40 and not higher than 70. Regarding a needle-shielding-type nozzle cap for a needle-equipped syringe, the type A durometer hardness of the nozzle cap can be not higher than 55, for instance, in order to make it even easier for a needle to pierce a needle piercing portion and in order to further assuredly prevent bending of the needle or the like.

Meanwhile, regarding a nozzle cap for a non-needle-equipped syringe, the type A durometer hardness of the nozzle cap can be not lower than 40, for instance, in order to further improve sealability at the time of storing the non-needle-equipped syringe with a nozzle thereof being covered by the nozzle cap and in order to even further assuredly prevent the nozzle cap from loosening and coming off from the nozzle.

The rubber hardness of the medical rubber part can be adjusted by changing the blending proportion of each raw material.

Regarding a sample of the medical rubber part molded from the medical rubber composition according to one or more embodiments of the present disclosure, the gas permeation rate (cc·cm/cm$^2$·sec·cmHg) per a thickness of 1 mm of the sample measured through the Method B (equal pressure method) stipulated in "Testing method for gas transmission rate through plastic film and sheeting" of the Japanese Industrial Standard JIS K7126-1987 can be, for instance, not lower than $2\times10^{-9}$, such as not lower than $4\times10^{-9}$, or not lower than $8\times10^{-9}$. Meanwhile, the gas permeation rate can be not higher than $8\times10^{-8}$, such as not higher than $4\times10^{-8}$, or not higher than $2\times10^{-8}$. The gas permeation rate can be adjusted to fall within the aforementioned range(s), by changing the blending proportion of each raw material. The gas permeation rate can be measured by, for example, using 02.

If the gas permeation rate falls within the aforementioned range(s), favorable gas permeability can be ensured. At the time of sterilization with EOG, the inside of the nozzle cap can be swiftly permeated with the EOG, whereby a nozzle and a needle can be sterilized in a short time. In addition, at the time of deaeration, residues such as ethylene oxide, ethylene glycol, and ethylene chlorohydrin can be swiftly reduced. Therefore, the sterilization time can be shortened, and productivity for the pre-fillable syringe can be improved. However, if the gas permeability is excessively high, permeation with an excessively increased amount of general gas may occur during a normal storage period that excludes the sterilization period. Consequently, sealability can deteriorate.

In addition, it can be possible to swiftly reduce an internal pressure applied inside the nozzle cap at the time of deaeration, whereby the nozzle cap can also be prevented from loosening and coming off from the nozzle.

The rubber part molded from the medical rubber composition according to one or more embodiments of the present disclosure can be suitably used as a nozzle cap of a pre-fillable syringe. The present disclosure can further encompass a pre-fillable syringe including the nozzle cap according to the present disclosure. In the present disclosure, the pre-fillable syringe can mean a syringe that is used as the prefilled syringe and that has not yet been filled with a drug solution. The pre-fillable syringe according to one or more embodiments of the present disclosure can be subjected to gas sterilization in a state where the nozzle cap is attached to the syringe.

The nozzle cap may be sometimes called by, for example, other names such as a needle cap, a needle shield, a rubber cap, a tip cap, a plunger tip, or a syringe sealing plug according to the manner of the attachment or other conditions.

Examples of the gas sterilization include treatment involving sterilization with vapor and treatment involving sterilization with ethylene oxide gas (EOG).

The treatment involving sterilization with EOG is a method for sterilizing a device in an ethylene oxide gas atmosphere. The concentration of the ethylene oxide gas can be, for instance, 400 mg/l to 1100 mg/l, such as 450 mg/l to 900 mg/l, or 500 mg/l to 700 mg/l. If the concentration of the ethylene oxide gas becomes excessively high, the concentration of the EOG remaining even after sterilization can tend to be high. The temperature during sterilization with EOG can be, for instance, 35° C. to 70° C., and the humidity (relative humidity) during the sterilization can be, for instance, not lower than 40% RH.

FIG. 1A is a cross-sectional view showing an example of a nozzle cap 9 according to one or more embodiments of the present disclosure and a nozzle 12, of a syringe barrel 11, that is to be covered by the nozzle cap 9. FIG. 1B is a cross-sectional view showing a state where the nozzle 12 is covered by the nozzle cap 9 in FIG. 1A.

The nozzle cap 9 can cover the nozzle 12 of the syringe barrel 11 of a non-needle-equipped syringe 10. The nozzle cap 9 can be formed as one member from the above medical rubber composition. The nozzle cap 9 can include a tubular portion 13 having an inner diameter D3 that is slightly smaller than an outer diameter D4 of the nozzle 12.

The tubular portion 13 can have: a one-end side (the upper-end side in the drawings) which is closed; and an other-end side (the lower-end side in the drawings) provided with an opening 14 through which the nozzle 12 is inserted into the tubular portion 13 so that the nozzle 12 is covered by the nozzle cap 9.

Figure 2B:
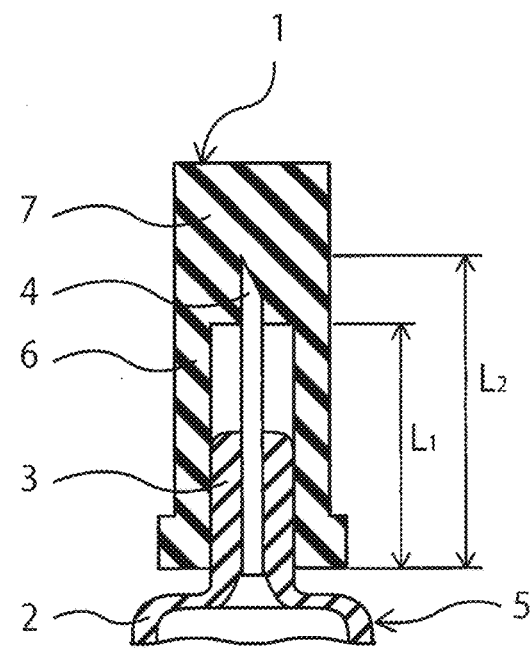

FIG. 2A is a cross-sectional view showing another example of the nozzle cap 1 according to one or more embodiments of the present disclosure and a nozzle 3, of a syringe barrel 2, that is to be covered by the nozzle cap 1. FIG. 2B is a cross-sectional view showing a state where the nozzle 3 is covered by the nozzle cap 1 in FIG. 2A.

The nozzle cap 1 can be for a needle-equipped syringe 5 in which a needle 4 is embedded in the nozzle 3 of the syringe barrel 2 in advance. The nozzle cap 1 can be, over the entirety thereof, for instance, formed as one member from the medical rubber composition. The nozzle cap 1 can include: a tubular portion 6 having an inner diameter D1 that is slightly smaller than an outer diameter D2 of the nozzle 3; and a needle piercing portion 7 formed so as to be contiguous with the one-end side (the upper-end side in the drawings) of the tubular portion 6.

The needle piercing portion 7 can be formed in a columnar shape so as to have an outer surface contiguous with the tubular portion 6. The other-end side (the lower-end side in the drawings) of the tubular portion 6 can be provided with an opening 8 through which the nozzle 3 is inserted into the tubular portion 6 so that the nozzle 3 is covered by the nozzle cap 1.

A dimension L1 in an axial direction of the tubular portion 6 from the one end thereof with which the needle piercing portion 7 can be formed so as to be contiguous and which is closed to the other end thereof on the opening 8 side is set to, with respect to a dimension L2 in the axial direction of the tubular portion 6 from the other end thereof on the above opening 8 side to the tip of the needle 4 in a state where the nozzle 3 is covered by the nozzle cap 1, satisfy L1<L2. With this setting, sealing can be performed in order to ensure liquid-tightness, gas-tightness, sterility, and the like while an end portion of the needle 4 pierces the needle piercing portion 7 by about 5 mm.

Each of the nozzle caps 1 and 9 can have a region with the smallest thickness. The region can be the tubular portion 13 in the example in FIG. 1A and FIG. 1B and can be the tubular portion 6 in the example in FIG. 2A and FIG. 2B. A thickness T2 of the tubular portion 13 and a thickness T1 of the tubular portion 6 can each be set to 1.0±0.5 mm, for instance.

If the thickness T1, T2 is beyond this range, permeation with gas or water vapor can be suppressed. Thus, can take time to perform sterilization with EOG, deaeration, or sterilization with vapor and subsequent drying, whereby the productivity for the pre-fillable syringe might be reduced.

In addition, it may be difficult or impossible to swiftly reduce an internal pressure generated inside the nozzle cap 1, 9 at the time of deaeration or at the time of sterilization with vapor and subsequent drying. Consequently, increase in the internal pressure might cause the nozzle cap 1, 9 to easily loosen and come off from the nozzle 3, 12, or might cause other inconveniences. Meanwhile, if the thickness T1, T2 is below the above range, the rigidity may become insufficient. Consequently, imperfection of plugging may become likely to occur at the time of plugging at which the nozzle 3, 12 is covered by the nozzle cap 1, 9, whereby reduction in the productivity for the pre-fillable syringe or other inconveniences might occur.

Unlike above, if the thickness T1, T2 is set to fall within the aforementioned range, favorable gas permeability can be imparted to the nozzle cap 1, 9. Consequently, in particular, at the time of sterilization with EOG, the inside of the nozzle cap 1, 9 can be swiftly permeated with EOG, whereby the nozzle 3, 12 and the needle 4 can be sterilized in a short time.

In addition, at the time of deaeration, residues such as ethylene oxide, ethylene glycol, and ethylene chlorohydrin can be swiftly removed. Therefore, the productivity for the pre-fillable syringe can be improved.

In addition, it can be possible to swiftly reduce an internal pressure generated inside the nozzle cap 1, 9 at the time of deaeration, whereby the nozzle cap 1, 9 can also be prevented from loosening and coming off from the nozzle 3, 12.

Further, an appropriate rigidity is imparted to the nozzle cap 1, 9. Consequently, imperfection of plugging can become less likely to occur at the time of plugging at which the nozzle 3, 12 is covered by the nozzle cap 1, 9, whereby the productivity for the pre-fillable syringe can be improved.

EXAMPLES

Hereinafter, the present disclosure will be described in detail by means of examples, but the present disclosure is not limited to the following examples, and any of modifications and implementation modes made within the scope of the gist of the present disclosure is included in the scope of the present disclosure.

[Preparation of Medical Rubber Compositions]

The materials indicated in Table 1 were kneaded to prepare medical rubber compositions. The kneading was performed at 20° C. for about 10 minutes by using an open roll.

| Medical rubber composition No. | 1 | 2 | 3 | 4 | 5 | 6 | 7 |
|---|---|---|---|---|---|---|---|
| (a) Isobutylene-isoprene rubber | 25 | 30 | 35 | 40 | 40 | 40 | 40 |
| (b) Diene-based rubber | 75 | 70 | 65 | 60 | 60 | 6-0 | 60 |
| Silica BET: 180 to 230 m$^2$/g | 5 | — | 5 | 0 | 3 | 5 | 7 |
| Silica BET: 130 to 190 m$^2$/g | — | 5 | — | — | — | — | — |
| Silica BET: 80 to 130 m$^2$/g | — | — | — | — | — | — | — |
| Talc | 15 | 15 | 15 | 15 | 15 | 15 | 15 |
| Sintered kaolin | 10 | 10 | 10 | 10 | 10 | 10 | 10 |
| Magnesium oxide | 1.5 | 1.5 | 1.5 | 1.5 | 1.5 | 1.5 | 1.5 |
| Carbon black | 0.2 | 0.2 | 0.2 | 0.2 | 0.2 | 0.2 | 0.2 |
| PEG4000 | 0.5 | 0.5 | 0.5 | 0.5 | 0.5 | 0.5 | 0.5 |
| Plasticizer | 2 | 2 | 2 | 2 | 2 | 2 | 2 |
| Triazine derivative | 1.00 | 1.00 | 1.00 | 1.00 | 1.00 | 1.00 | 1.00 |
| Peroxide-based crosslinking agent | 0.2 | 0.2 | 0.2 | 0.2 | 0.2 | 0.2 | 0.2 |
| Total | 135.40 | 135.40 | 135.40 | 130.40 | 133.40 | 135.40 | 137.40 |
| Inorganic filler content (wt %) | 23.26 | 23.26 | 23.26 | 20.32 | 22.11 | 23.26 | 24.38 |
| O2 gas permeability cc · cm/cm$^2$ · sec · cmHg | 4.77E−09 | 3.50E−09 | 3.09E−09 | 2.60E−09 | 2.60E−09 | 2.60E−09 | 2.60E−09 |
| Relative evaluation | ○ | ○ | ○ | ○ | ○ | ○ | ○ |
| Oozing-substance performance | | | | | | | |
| Potassium permanganate reducing substance (mL/100 mL) | 0.6 | 0.52 | 0.49 | 0.48 | 0.48 | 0.48 | 0.48 |
| Relative evaluation | × | × | ○ | ○ | ○ | ○ | ○ |
| Molded product strength (MPa) | 5.105 | 7.25 | 5.401 | 4.113 | 5.19 | 5.089 | 6.37 |
| Relative evaluation | ○ | ○ | ○ | × | ○ | ○ | ○ |
| Moldability (weld line generation) | ○ | ○ | ○ | ○ | ○ | ○ | ○ |

| Medical rubber composition No. | 8 | 9 | 10 | 11 | 12 | 13 |
|---|---|---|---|---|---|---|
| (a) Isobutylene-isoprene rubber | 40 | 40 | 40 | 45 | 55 | 70 |
| (b) Diene-based rubber | 60 | 60 | 60 | 55 | 45 | 30 |
| Silica BET: 180 to 230 m$^2$/g | 10 | — | — | 5 | 5 | 5 |
| Silica BET: 130 to 190 m$^2$/g | — | 5 | — | — | — | — |
| Silica BET: 80 to 130 m$^2$/g | — | — | 5 | — | — | — |
| Talc | 15 | 15 | 15 | 15 | 15 | 15 |
| Sintered kaolin | 10 | 10 | 10 | 10 | 10 | 10 |
| Magnesium oxide | 1.5 | 1.5 | 1.5 | 1.5 | 1.5 | 1.5 |
| Carbon black | 0.2 | 0.2 | 0.2 | 0.2 | 0.2 | 0.2 |
| PEG4000 | 0.5 | 0.5 | 0.5 | 0.5 | 0.5 | 0.5 |
| Plasticizer | 2 | 2 | 2 | 2 | 2 | 2 |
| Triazine derivative | 1.00 | 1.00 | 1.00 | 1.00 | 1.00 | 1.00 |
| Peroxide-based crosslinking agent | 0.2 | 0.2 | 0.2 | 0.2 | 0.2 | 0.2 |
| Total | 140.40 | 135.40 | 135.40 | 135.40 | 135.40 | 135.40 |
| Inorganic filler content (wt %) | 26.00 | 23.26 | 23.26 | 23.26 | 23.26 | 23.26 |
| O2 gas permeability cc · cm/cm$^2$ · sec · cmHg | 2.60E−09 | 2.60E−09 | 2.60E−09 | 2.20E−09 | 1.62E−09 | 7.39E−10 |
| Relative evaluation | ○ | ○ | ○ | ○ | × | × |
| Oozing-substance performance | | | | | | |
| Potassium permanganate reducing substance (mL/100 mL) | 0.48 | 0.48 | 0.48 | 0.45 | 0.4 | 0.3 |
| Relative evaluation | ○ | ○ | ○ | ○ | ○ | ○ |
| Molded product strength (MPa) | 7.402 | 7.551 | 4.82 | 5.23 | 5.309 | 5.412 |
| Relative evaluation | ○ | ○ | × | ○ | ○ | ○ |
| Moldability (weld line generation) | × | ○ | ○ | ○ | ○ | ○ |

Unit of blending amount: part by mass

The details of blending materials that were used are as follows.

Isobutylene-isoprene rubber: HT-1066 (chlorinated isobutylene-isoprene rubber)

Diene-based rubber: poly butadiene rubber BR-1220

Silica: Nipsil (BET specific surface area 80 m$^2$/g to 130 m$^2$/g, 130 m$^2$/g to 190 m$^2$/g, 180 m$^2$/g to 230 m$^2$/g)

Magnesium oxide: Kyowamag MF

Talc: MISTRON

Sintered kaolin: SATINTONE

PEG4000: polyoxyethylene glycol (average molecular weight: 3100, solidifying point: 55° C.)

Carbon black: Thermal MT

Peroxide-based crosslinking agent: PERHEXA 25B-40

Triazine derivative: 6-dibutylamino-1,3,5-triazine-2,4-dithiol

[Evaluation Method]

(1) Gas Permeability Coefficient (cc·cm/cm$^2$·sec·cmHg)

Test pieces for measurement of gas permeability coefficient were produced from the obtained medical rubber compositions, and the gas permeability coefficients of the test pieces were measured. The measurement was performed through a differential-pressure method according to JIS-K6275-1 by using GTR-30XASR manufactured by the GTR Corporation.

Test gas: O$_2$

Measurement samples: the rubber compositions were press-molded at 180° C. for 6 minutes, to produce slabs having thicknesses of 0.5 mm to 1.0 mm.

<Relative Evaluation>

In the table, in the case where an O$_2$ permeability coefficient was not smaller than 2.0×10$^9$ (cc·cm/cm$^2$·sec·cmHg), "○" (good) was given as an evaluation result. Meanwhile, in the case where an O$_2$ permeability coefficient was smaller than 2.0'10$^9$ (cc·cm/cm$^2$·sec·cmHg), "x" (poor) was given as an evaluation result.

(2) Oozing-Substance Test

Measurement samples; the rubber compositions obtained as above by blending were press-molded at 180° C. for 6 minutes, to produce 2-mm slabs. Each slab was punched to obtain a test sample by using a puncher having a diameter of 17 mm.

The produced sample was tested according to the method in "Extractable substances" described in "7.03 Test for Rubber Closure for Aqueous Infusions" of the 17th edition of the Japanese Pharmacopoeia. Adaptation conditions are as follows.

Properties of test solution: colorless and clear

Ultraviolet transmissivity: a transmissivity at each of a wavelength of 430 nm and a wavelength of 650 nm with a layer length of 10 mm being not lower than 99.0%.

Ultraviolet absorption spectrum: an absorbance at a wavelength of 220 nm to 350 nm being not higher than 0.20.

pH: the difference between a test solution and a blank test solution being not larger than 1.0.

Zinc: the absorbance of the sample solution being not higher than the absorbance of a standard solution Potassium permanganate reducing substance: not higher than 2.0 mL/100 mL (according to a standard in the Japanese Pharmacopoeia)

Post-evaporation residue: not larger than 2.0 mg

<Relative Evaluation>

In the table, in the case where a concentration of the potassium permanganate reducing substance was lower than 0.5 mUl00 mL, "c" (good) was given as an evaluation result.

Meanwhile, in the case where a concentration of the potassium permanganate reducing substance was not lower than 0.5 mL/100 mL, "x" (poor) was given as an evaluation result.

(3) Molded Product Strength

<Tensile Property Test>

The rubber compositions obtained as above by blending were formed as sheets having thicknesses of 2 mm through press-molding under conditions of 180° C. and 6 minutes. Each sheet was punched, and a No. 3 dumbbell-shaped test piece stipulated in "Rubber, vulcanized or thermoplastic—Determination of tensile stress-strain properties" of the Japanese Industrial Standard JIS K6251: 2010 was produced. Then, a tensile test defined in the above standard was performed on the test piece in an environment of a temperature of 23° C. and a relative humidity of 55%, and a tensile strength TS (MPa), an elongation at break Eb (%), and a tensile stress at 100%-elongation (100% modulus) of the test piece were obtained. A molded-product strength of the test piece was evaluated by using the tensile strength TS (MPa).

(4) Moldability (Weld Line Generation)

Caps each having the shape shown in FIG. 1A were produced through press-molding under conditions of 180° C. and 6 minutes. Then, the side surface of each cap was visually checked. In the case where a weld line (rubber flow pattern) was observed, the moldability was determined as "x" (poor). Meanwhile, in the case where no weld line was observed, the moldability was determined as "c" (good).

The results of the tests for gas permeability, oozing-substance performance, molded product strength, and moldability are collectively indicated in Table 1.

From Table 1, it is found that each medical rubber part formed from the medical rubber composition according to the present disclosure has excellent non-oozing characteristics and an excellent gas permeability.

The present disclosure has been made in view of the above circumstances in the background section, and an object of one or more embodiments of the present disclosure, among multiple objects, can be to provide a medical rubber composition having gas permeability so as to be suitable for gas sterilization while maintaining non-oozing characteristics. Another object of one or more embodiments of the present disclosure is to provide a medical rubber composition having a favorable moldability and a high molding strength. Usage of the medical rubber composition according to the present disclosure can lead to obtaining of: a medical rubber composition having gas permeability so as to be excellent in gas sterilization while maintaining non-oozing characteristics; and a medical rubber part in which the medical rubber composition has been used. The medical rubber composition according to one or more embodiments of the present disclosure can be used to obtain a medical rubber part having a high moldability and a high molded-product strength. Usage of the medical rubber composition according to one or more embodiments of the present disclosure can lead to obtaining of: a nozzle cap having gas sterilizability so as to be excellent in gas sterilization while maintaining non-oozing characteristics; and a pre-fillable syringe in which the nozzle cap has been used.

Aspect (1) of the present disclosure is directed to a medical rubber composition containing: (a) an isobutylene-isoprene rubber; (b) a diene-based rubber; and a silica having a BET specific surface area not lower than 130 m$^2$/g, wherein an amount of (a) the isobutylene-isoprene rubber contained in 100 parts by mass of a rubber component composed of (a) the isobutylene-isoprene rubber and (b) the diene-based rubber is larger than 30 parts by mass and smaller than 55 parts by mass.

Aspect (2) of the present disclosure is directed to the medical rubber composition according to aspect (1) of the present disclosure, wherein the amount of (a) the isobutylene-isoprene rubber contained in 100 parts by mass of the rubber component composed of (a) the isobutylene-isoprene rubber and (b) the diene-based rubber is not smaller than 31 parts by mass and not larger than 54 parts by mass.

Aspect (3) of the present disclosure is directed to the medical rubber composition according to aspect (1) or (2) of the present disclosure, wherein (b) the diene-based rubber contains polybutadiene.

Aspect (4) of the present disclosure is directed to the medical rubber composition according to any one of aspects (1) to (3) of the present disclosure, wherein the BET specific surface area of the silica is not lower than 160 $m^2/g$ and not higher than 240 $m^2/g$.

Aspect (5) of the present disclosure is directed to the medical rubber composition according to any one of aspects (1) to (4) of the present disclosure, wherein an amount of the silica contained per 100 parts by mass of the rubber component is not smaller than 2 parts by mass and smaller than 10 parts by mass.

Aspect (6) of the present disclosure is directed to the medical rubber composition according to any one of aspects (1) to (5) of the present disclosure, wherein an amount of the silica contained per 100 parts by mass of the rubber component is 3 parts by mass to 9 parts by mass.

Aspect (7) of the present disclosure is directed to the medical rubber composition according to any one of aspects (1) to (6) of the present disclosure, the medical rubber composition further containing (c1) a peroxide-based crosslinking agent and (c2) a triazine derivative.

Aspect (8) of the present disclosure is directed to a medical rubber part molded from the medical rubber composition according to any one of aspects (1) to (7) of the present disclosure.

Aspect (9) of the present disclosure is directed to a nozzle cap for a pre-fillable syringe, the nozzle cap being molded from the medical rubber composition according to any one of aspects (1) to (7) of the present disclosure.

Aspect (10) of the present disclosure is directed to a pre-fillable syringe including the nozzle cap according to aspect (9) of the present disclosure.

Aspect (11) of the present disclosure is directed to the pre-fillable syringe according to aspect (10) of the present disclosure, wherein the nozzle cap has been subjected to gas sterilization in a state of being attached to the syringe.

Aspect (12) of the present disclosure is directed to the medical rubber composition according to any one of aspects (1) to (11) of the present disclosure wherein a mass ratio of the peroxide-based crosslinking agent (c1) to the triazine derivative (c2) is in a range of 00.5 to 0.5.

Aspect (13) of the present disclosure is directed to the medical rubber composition according to any one of aspects (1) to (12) of the present disclosure wherein the range of the mass ratio of the peroxide-based crosslinking agent (c1) to the triazine derivative (c2) is 0.15 to 0.2.

Aspect (14) of the present disclosure is directed to the medical rubber composition according to any one of aspects (1) to (13) of the present disclosure wherein the medical rubber composition further comprises a filler other than the silica.

Aspect (15) of the present disclosure is directed to the medical rubber composition according to any one of aspects (1) to (14) of the present disclosure wherein the filler other than silica is an inorganic filler forming a content of the medical rubber composition in a range from 10% (by mass) to 45% (by mass).

Aspect (16) of the present disclosure is directed to the medical rubber composition according to any one of aspects (1) to (15) of the present disclosure wherein the range of the content of the inorganic filler of the medical rubber composition is from 20% (by mass) to 35% (by mass).

Aspect (17) of the present disclosure is directed to the medical rubber composition according to any one of aspects (1) to (16) of the present disclosure wherein the inorganic filler excludes carbon black.

Aspect (18) of the present disclosure is directed to the medical rubber composition according to any one of aspects (1) to (17) of the present disclosure wherein the filler other than the silica replaces the silica as a component of the medical rubber composition.

Aspect (19) of the present disclosure is directed to the medical rubber composition according to any one of aspects (1) to (18) of the present disclosure wherein an amount of the filler other than silica contained per 100 parts by mass of the medical rubber composition is in a range of 10 parts by mass to 40 parts by mass.

Aspect (20) of the present disclosure is directed to the medical rubber composition according to any one of aspects (1) to (19) of the present disclosure wherein the range of the amount of the filler other than silica contained per 100 parts by mass of the medical rubber composition is 20 parts by mass to 30 parts by mass.

What is claimed is:

1. A medical rubber composition comprising:
   (a) an isobutylene-isoprene rubber;
   (b) a diene-based rubber; and
   a silica having a BET specific surface area not lower than 130 $m^2/g$, wherein
   an amount of (a) the isobutylene-isoprene rubber contained in 100 parts by mass of a rubber component composed of (a) the isobutylene-isoprene rubber and (b) the diene-based rubber is larger than 30 parts by mass and smaller than 55 parts by mass,
   an amount of the silica contained per 100 parts by mass of the rubber component is 3 parts by mass to 9 parts by mass, and
   an $O_2$ permeability coefficient of a test slab of the medical rubber composition is at least $2.0 \times 10^{-9}$ cc·cm/$cm^2$·sec·cmHg and a concentration of potassium permanganate reducing substance in an oozing-substance test of a test sample of the medical rubber composition is lower than 0.5 mL/100 mL,
   wherein the test slab is prepared by press-molding the medical rubber composition at 180° C. for 6 minutes and has a thicknesses of 0.5 mm to 1.0 mm, and the test sample is prepared by press-molding the medical rubber composition at 180° C. for 6 minutes and having a diameter of 17 mm and a thickness of 2 mm.

2. The medical rubber composition according to claim 1, wherein
the amount of (a) the isobutylene-isoprene rubber contained in 100 parts by mass of the rubber component composed of (a) the isobutylene-isoprene rubber and (b) the diene-based rubber is not smaller than 31 parts by mass and not larger than 54 parts by mass.

3. The medical rubber composition according to claim 1, wherein
(b) the diene-based rubber contains polybutadiene.

4. The medical rubber composition according to claim 1, wherein
the BET specific surface area of the silica is not lower than 160 m$^2$/g and not higher than 240 m$^2$/g.

5. The medical rubber composition according to claim 1, wherein
the amount of the silica contained per 100 parts by mass of the rubber component is not smaller than 5 parts by mass and smaller than 7 parts by mass.

6. The medical rubber composition according to claim 1, wherein
the medical rubber composition further comprises (c1) a peroxide-based crosslinking agent and (c2) a triazine derivative.

7. The medical rubber composition according to claim 6, wherein
a mass ratio of the peroxide-based crosslinking agent (c1) to the triazine derivative (c2) is in a range of 0.05 to 0.5.

8. The medical rubber composition according to claim 7, wherein
the range of the mass ratio of the peroxide-based crosslinking agent (c1) to the triazine derivative (c2) is 0.15 to 0.2.

9. The medical rubber composition according to claim 1, wherein
the medical rubber composition further comprises a filler other than the silica.

10. The medical rubber composition according to claim 9, wherein
the filler other than silica is an inorganic filler forming a content of the medical rubber composition in a range from 10% (by mass) to 45% (by mass).

11. The medical rubber composition according to claim 10, wherein
the range of the content of the inorganic filler of the medical rubber composition is from 20% (by mass) to 35% (by mass).

12. The medical rubber composition according to claim 10, wherein
the inorganic filler excludes carbon black.

13. The medical rubber composition according to claim 9, wherein
the filler other than the silica replaces the silica as a component of the medical rubber composition.

14. The medical rubber composition according to claim 9, wherein
an amount of the filler other than silica contained per 100 parts by mass of the medical rubber composition is in a range of 10 parts by mass to 40 parts by mass.

15. The medical rubber composition according to claim 14, wherein
the range of the amount of the filler other than silica contained per 100 parts by mass of the medical rubber composition is 20 parts by mass to 30 parts by mass.

16. A medical rubber part molded from the medical rubber composition according to claim 1.

17. A nozzle cap for a pre-fillable syringe, the nozzle cap being molded from the medical rubber composition according to claim 1.

18. A pre-fillable syringe comprising the nozzle cap according to claim 17.

19. The pre-fillable syringe according to claim 18, wherein
the nozzle cap has been subjected to gas sterilization in a state of being attached to the syringe.

* * * * *